US00PP08707P

United States Patent [19]

Knottenbelt et al.

[11] Patent Number: Plant 8,707

[45] Date of Patent: May 3, 1994

[54] APPLE TREE NAMED 'BELLE COX'

[76] Inventors: Robert Knottenbelt; Meta Knottenbelt, both of Poukawa Orchards, RD11, Hastings, New Zealand

[21] Appl. No.: 936,820

[22] Filed: Aug. 28, 1992

[51] Int. Cl.[5] ..... A01H 5/00
[52] U.S. Cl. ..... Plt./34.1
[58] Field of Search ..... Plt. 34.1

[56] References Cited

PUBLICATIONS

R. M. Brooks et al (1972) Register of New Fruit and Nut Varieties p. 15.

Application for Plant Selectors' Rights and Protective Direction.
Technical Questionnaire.
Objective Description of Variety.
Grant No. 609, Aug. 28, 1991.

*Primary Examiner*—James R. Feyrer
*Assistant Examiner*—Bruce R. Campbell
*Attorney, Agent, or Firm*—Quarles & Brady

[57] ABSTRACT

A new and distinct variety of apple tree called Belle Cox is a mutation of Bledisloe Cox's Orange Pippin variety, and is characterized by its fruit which has broad red stripes of 50–70% on a yellow-green background after ten weeks in cool storage. Belle Cox also blooms 5–7 days later than its parent, Cox's Orange Pippin (Bledisloe).

2 Drawing Sheets

SUMMARY OF THE INVENTION

The present invention relates to a new and distinct apple variety. The new cultivar is designated 'Belle Cox' and is a mutation of the Bledisloe Cox's Orange Pippin variety.

After the variety was discovered by the Petitioners at Poukawa Orchards it was asexually reproduced in 1984 and planted at the Petitioners property, Poukawa Orchards, Hastings, New Zealand by budding on to rootstock of the M793 variety. The fruit was first observed on the reproduced plants in 1987. Asexual propagation by budding shows that the unique combination of characteristics and distinctive colour come true to form and are established and transmitted through succeeding propagations.

BRIEF DESCRIPTION OF THE DRAWINGS

The accompanying photograph shows typical specimens of the fruit of the new variety as depicted in colours as nearly true as is reasonably possible to make the same in a colour illustration of this character.

DETAILED DESCRIPTION

Figure 1:
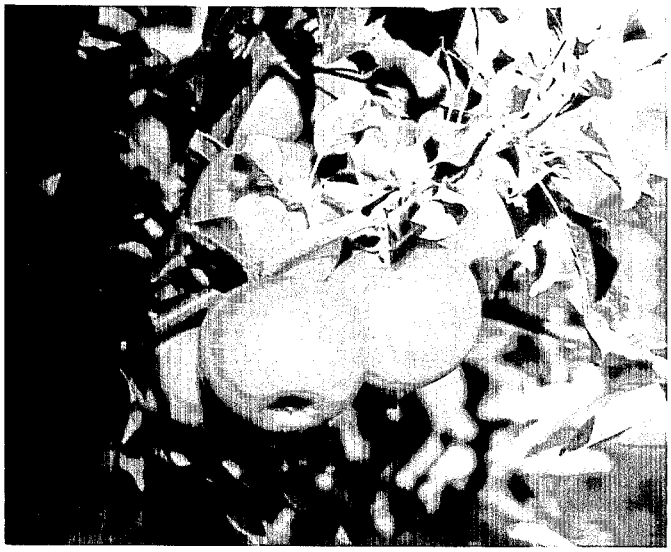
FIG. 1: shows a typical collection of mature Bell Cox fruit on the tree.
Figure 2:
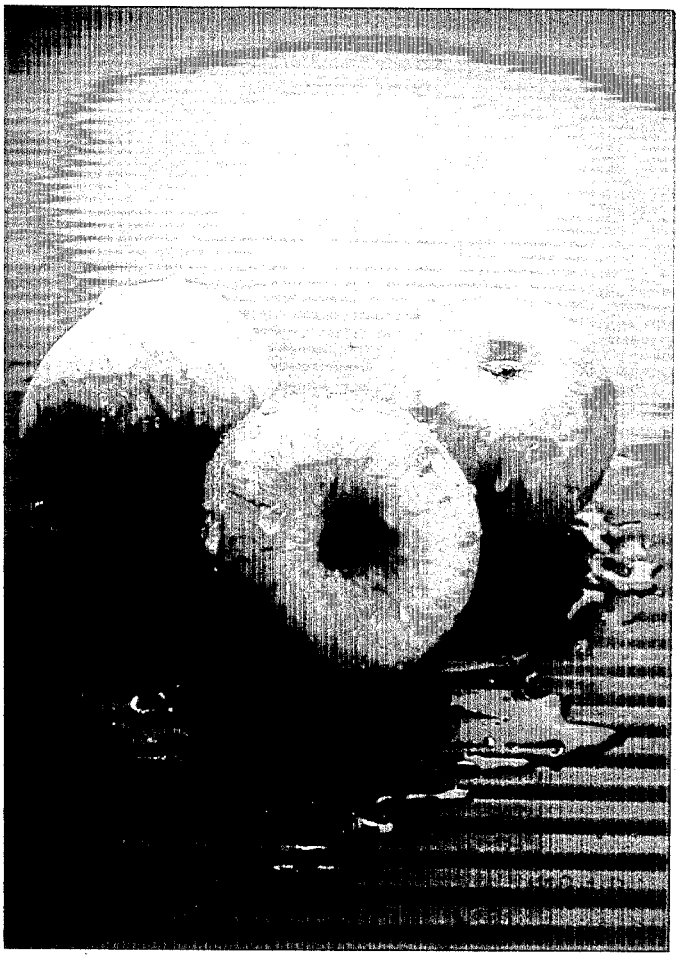
FIG. 2: shows a typical collection of mature Cox's Orange Pippin (Bledisloe), the parental plant of Belle Cox.

The distinctive characteristics of this new apple cultivar described below were observed in the 1990 and 1991 seasons on M793 root stock at the Petitioners' property in Hastings. The trees were in their second year of fruiting.

The colour designations hereinafter set forth are according to the Munsell Colour System using a Minolta colour meter. The fruit of the Belle Cox and Cox Orange Pippin (Bledisloe) were measured for colour after 10 weeks in cool storage.

Belle Cox is similar to its parent Bledisloe Cox's Orange Pippin but has broad red stripes (7.5R3/2) of 50–70% on a yellow green background as compared to Cox's Orange Pippin (Bledisloe) which is orange shaded with a dull red (10R4/6) thinner stripes of 10–30% on a yellow-green background (10Y7/8). Cox's Orange Pippin (Bledisloe) is essentially the same as Cox's Orange Pippin save for the fruit colour, in that Cox's Orange Pippin has proportionally more fruit with a dull red stripe of 5–10%. Belle Cox also blooms 5–7 days later than Cox's Orange Pippin (Bledisloe). Belle Cox has a lower incidence of russet and stem end cracking than Cox's Orange Pippin (Bledisloe) which results in a better packout (87% in 1992 off applicants' property as compared to 50% for Cox's Orange Pipin in the same year).

Tree: Medium vigour, spreading habit; predominance of bearing on spurs; medium spur density; medium to high branching density; on trees of seven years of age on M793 root stock, the canopy height is approximately 4 meters and the canopy width 3 meters; terminal growth is 1 meter on M793 root stock; the trees are annual bearing under a good management regime; medium thinning requirement on M793 root stock; similar productivity to Cox's Orange Pippin (Bledisloe).

*Dormant one year old shoot (observed in winter on trees at least three years old)*.—Weak pubescence on upper half; medium thickness; few lenticels; reddish brown colour on the sunny side; medium bud size; pointed bud tip; position of bud relative to axis; adpressed; large bud support; dormant fruit bud shape (on spurs), conical-ovoid; color of bark in brown 2.5YR3/1.

Flower: Colour of bud just before the flower opens, deep rose; time of flowering (10% of flowers), medium. Observation of flowers at start of anther dehiscence, moderately cupped shape; large size; position of margin of petals, touching;

Leaf: Medium time of bud burst. (Mature leaves observed in summer when they form middle one third of an upright growing shoot on the outside of the tree pose of leaf, outwards; medium size; length from 4th to 6th fully expanded leaf, 94 mm; width from 4th to 6th fully expanded leaf; 45 mm; medium length/-width ratio of blade; concave shape in cross-section; serrate indentation of margin; medium glossiness on upper side; weak pubescence on lower side; medium petiole length; small stipule size; colour of upper side of leaf in May in Hastings is green 5GY5/3; colour of underside of leaves in May in Hastings is green 7.5GY3/2.

Fruit:

*Size.*—Large; length 59 mm, breadth 79 mm.

*Shape.*—Short truncate; asymmetric in side view; no crowning at distal end.

*Eye.*—Closed; medium size.

*Eye basin.*—Medium depth; medium width; no ribbing.

*Sepals.*—Medium length; touching at base.

*Stalk.*—Short; medium thickness.

*Stalk cavity.*—Medium depth; medium width.

*Skin.*—Ribbing, absent; smooth surface; greasiness, absent; cracking tendency, absent; medium skin thickness; yellow green ground colour; colour measurements unable to be taken due to predominance of red stripe.

*Over colour.*—50–70% striped red over colour (7.5R3/6); low amount of russet around stalk.

*Lenticels.*—Small size.

*Flesh.*—Firm; white; at harvest medium texture; medium juciness; the colour at ten weeks in storage is 10Y8/6. The flesh colour of Cox's Orange Pippin (Bledisloe) at ten weeks in storage is 10Y8/3.

*Flavour.*—Low sweetness; medium acidity.

*Calyx tube.*—Short length; medium width; U or V shaped.

*Sinus.*—Closed.

*Distinctiveness of core line.*—Medium when observed in cross section.

*Aperture of locules.*—Open in cross section.

*Central cavity.*—Absent in cross section.

*Ripening.*—At Cox's Orange Pippin, in Hastings harvest was between 13 February–6 March in 1991.

*Seed.*—Medium size; brown colour when dry; colour at ten weeks of storage is 2.5YR2/3.

We claim:

1. A new and distinct variety of apple tree which is a mutation of the Bledisloe Cox's Orange Pippin variety, substantially as shown and described characterised by its striped red overcolour.

* * * * *